(12) United States Patent
Di Costanzo et al.

(10) Patent No.: US 8,377,472 B1
(45) Date of Patent: Feb. 19, 2013

(54) ORALLY DISPERSIBLE TABLET WITH LOW FRIABILITY AND METHOD FOR PREPARING SAME

(75) Inventors: Laurent Di Costanzo, Fontenay sous Bois (FR); Edouard André Gendrot, Garnay (FR); Mathieu Ernest Jean-Baptiste Di Costanzo, Opio (FR); Charles André Chauveau, Valbonne (FR)

(73) Assignee: Ethypharm, Saint-Cloud Cedex (FR)

( * ) Notice: Subject to any disclaimer, the term of this patent is extended or adjusted under 35 U.S.C. 154(b) by 0 days.

(21) Appl. No.: 09/914,544

(22) PCT Filed: Feb. 29, 2000

(86) PCT No.: PCT/FR00/00495
§ 371 (c)(1),
(2), (4) Date: Mar. 19, 2002

(87) PCT Pub. No.: WO00/51568
PCT Pub. Date: Sep. 8, 2000

(30) Foreign Application Priority Data

Mar. 1, 1999 (FR) ..................................... 99 02516

(51) Int. Cl.
*A61K 9/20* (2006.01)
(52) U.S. Cl. ........................................................ 424/464
(58) Field of Classification Search .................. 424/464, 424/439, 465, 470, 488, 400, 468, 489, 484, 424/485
See application file for complete search history.

(56) References Cited

U.S. PATENT DOCUMENTS

| | | | |
|---|---|---|---|
| 4,292,017 A | 9/1981 | Doepel | |
| 4,684,534 A * | 8/1987 | Valentine | 424/441 |
| 4,832,880 A | 5/1989 | Staniforth | |
| 5,017,122 A | 5/1991 | Staniforth | |
| 5,464,632 A | 11/1995 | Cousin et al. | |
| 5,643,630 A | 7/1997 | Hinzpeter et al. | |
| 5,725,880 A * | 3/1998 | Hirakawa et al. | 424/480 |
| 6,079,968 A * | 6/2000 | Schmitz et al. | 425/96 |
| 6,106,861 A | 8/2000 | Chauveau et al. | |
| 6,391,337 B2 * | 5/2002 | Hunter et al. | 424/474 |
| 6,465,009 B1 * | 10/2002 | Liu et al. | 424/464 |

FOREIGN PATENT DOCUMENTS

| | | |
|---|---|---|
| DE | 43 18 577 A1 | 12/1994 |
| EP | 0 650 826 B1 | 11/1994 |
| EP | 0 676 280 A1 | 11/1995 |
| EP | 0 745 382 A1 | 12/1996 |
| EP | 0 914 818 A1 | 5/1999 |
| EP | 0 914 818 A1 | 12/1999 |
| EP | 0 815 931 B1 | 9/2000 |
| EP | 1 070 497 A1 | 1/2001 |
| FR | 2 679 451 A1 | 7/1991 |
| FR | 2 766 089 A1 | 7/1997 |
| WO | WO 99/04763 A1 | 7/1998 |
| WO | WO 00/27357 | 5/2000 |

OTHER PUBLICATIONS

"Friability of Tablets" The French Pharmacopoeia $19^{th}$ Edition, V.5. 1., Jan. 1993.
Remington's Pharmaceutical Sciences, $18^{th}$ Edition, pp. 1639-1640 (1990).
Pharmaceutical Dosage Forms, vol. 2, pp. 246-247 (1981).
Remington's Pharmaceutical Sciences, $18^{th}$ Edition, pp. 1666-1669 (1990).
Remington's Pharmaceutical Sciences, $18^{th}$ Edition, p. 593 (1990).
Aldrich Catalogue, p. 1146.
Abstract of Symposium regarding EP 00 907 743.9 (with translation).
Experimental Data regarding EP 00 907 743.9.
Requete Auxiliaire regarding EP 00 907 743.9.

* cited by examiner

*Primary Examiner* — Paul Dickinson
(74) *Attorney, Agent, or Firm* — RatnerPrestia

(57) ABSTRACT

The invention concerns a rapidly disintegrating tablet similar to those designed to disintegrate in the mouth on contact with saliva in less than 30 seconds, forming an easy-to-swallow suspension, and based on an active substance in the form of coated microcrystals or microgranules and a mixture of excipients including at least a disintegrating agent, a soluble agent and a lubricating agent. The invention is characterized in that the lubricating agent is in powder form and is distributed at least for the greater part on the tablet surface and its friability, measured as specified in the French Pharmacopoeia (10th Edition, V.5.1—Friability of Tablets, January 1993), is less than 1%, and preferably less than 0.5%, whereby said tablet can be packaged by standard processes, and has the required and adequate hardness to enable it to be removed with ease from the blister pack in which it is packaged, by perforating the seal thereof by pushing the tablet, with a substantially reduced risk of the tablet breaking during removal. The invention also concerns the method for producing said tablet.

24 Claims, No Drawings

ORALLY DISPERSIBLE TABLET WITH LOW FRIABILITY AND METHOD FOR PREPARING SAME

The invention concerns an orally dispersible tablet, that is to say a rapidly disintegrating tablet similar to those designed to disintegrate in the mouth on contact with saliva, preferably in less than 40 seconds or even in less than 30 seconds. The invention also concerns the process for producing this tablet.

Previously known rapidly disintegrating tablets, for example those described by the Applicant Company in FR 97 09233, FR 98 14034, FR 92 08642 and FR 91 09245, often display high friability, and this requires special precautions when they are being transported and packaged, limiting the choice of packaging used.

The aim of this invention is primarily to provide tablets of the type concerned, having a pleasant taste and with a friability (measured as specified in the French Pharmacopoeia (10th Edition, V.5.1—Friability of Tablets, January 1993), i.e. a hardness and resistance to abrasion, which enable them to be packaged and transported by conventional means, as well as to ensure ease of use by the patient.

The Applicant has found, surprisingly and unexpectedly, that it was possible to incorporate all these properties, some of which may appear incompatible with others, in a rapidly disintegrating tablet similar to those which are designed to disintegrate in the mouth in less than 30 seconds on contact with saliva, forming an easily-swallowed suspension. These tablets are based on an active substance in the form of coated microcrystals or microgranules and a mixture of excipients including at least one disintegrating agent, a soluble agent and a lubricating agent, and prior to compression at least the greater part of the lubricating agent is no longer present in the mixture of excipients, but is brought into contact with the outer surface of the mass that will form the subsequent tablet.

A tablet of this sort may be packaged by standard operations, that is to say using conventional industrial machinery. The tablet is sufficiently hard to enable it to be removed easily from the blister in which it is packaged, by tearing, perforating or breaking the seal of the blister pack by pushing the tablet, with a substantially reduced risk of the tablet breaking.

The tablet according to this invention is therefore characterized in that a major amount of the lubricating agent which is used in its composition and which is in powder form, is distributed on the tablet surface, and by the fact that its friability, measured as specified in the French Pharmacopoeia (10th Edition, V.5.1—Friability of Tablets, January 1993), is less than 1%, and preferably less than 0.5%.

The lubricating agent is chosen from pharmaceutically acceptable lubricating agents which have a melting point of at least 35° C. and preferably higher than 50° C.

Preferably, the lubricating agent is selected from the group comprising in particular magnesium stearate, sodium stearyl fumarate, stearic acid, micronized polyoxyethylene glycol (micronized Macrogol 6000), leucine, sodium benzoate and their mixtures.

The quantity of lubricating agent employed in the tablet according to this invention is in the range 0.2 to 10 parts per thousand (weight of lubricating agent/total weight of tablet), and is preferably in the range 3 to 6 parts per thousand.

According to a preferred embodiment of the tablet according to the invention, the entire amount of lubricating agent is distributed on the outer surface of the tablet.

It must be stressed that this quantity is up to ten times less than that which has been required in known rapidly disintegrating tablets of the type in question, in which the lubricating agent is distributed within the excipient.

The particle size distribution of the lubricating agent in powder form is such that its constituent particles adhere to a surface when it is sprayed thereon.

According to a preferred embodiment, this particle size is less than 30 microns and is preferably less than 10 microns.

The disintegrating agent is selected from the group including in particular cross-linked sodium carboxymethylcellulose, known in the industry as croscarmellose, crospovidone and their mixtures.

The soluble agent is preferably a diluent soluble agent with binding properties, such as, in particular, a polyol. This soluble agent can advantageously be selected in accordance with the description given in patent applications FR 97 09233 or FR 98 14034 in the name of the Applicant.

According to a preferred embodiment of the tablet according to the invention, the mixture of excipients includes a permeabilising agent, a solubilising agent, sweeteners, flavors and coloring agents.

The permeabilising agent used may be a compound selected from the group including in particular silicas with a high affinity for aqueous solvents, such as precipitated silica, better known by the brand name SYLOID®, colloidal silica better known by the name of AEROSIL® 200, maltodextrines, betacyclodextrines and their mixtures.

The sweetener may be chosen from the group including in particular aspartame, potassium acesulfam, sodium saccharinate, neohesperidine didrochalcone and their mixtures.

The flavorings and coloring agents are those normally used in pharmaceutical manufacture for the production of tablets.

Any active substance which can be employed in rapidly disintegrating tablets of the type in question may be used to advantage in the tablets concerned in this invention.

With regard to active substances, at least one of those may be used from the group including gastrointestinal sedatives, antacids, analgesics, anti-inflammatory drugs, coronary vasodilators, peripheral and cerebral vasodilators, anti-infective agents, antibiotics, antiviral agents, antiparasitic agents, anti-cancer drugs, anxiolytics, neuroleptics, central nervous system stimulants, antidepressants, anti-histamine substances, anti-diarrhoeal substances, laxatives, dietary supplements, immunodepressants, cholesterol-lowering agents, hormones, enzymes, antispasmodics, anti-anginal drugs, drugs acting on heart rhythm, drugs used in the treatment of arterial hypertension, anti-migraine substances, drugs affecting coagulation of the blood, anti-epileptic substances, muscle relaxants, drugs used in the treatment of diabetes, drugs used in the treatment of thyroid disorders, diuretics, appetite suppressants, anti-asthmatic drugs, expectorants, antitussives, mucus regulators, decongestants, hypnotics, anti-nausea substances, haematopoietic agents, substances inducing the elimination of uric acid, plant extracts, contrast media.

In the case of 17 mm diameter tablets according to the invention, the hardness is advantageously greater than 20 N, and preferably greater than 40 N, or more preferably still, greater than 80 N. This hardness is in all cases at least equal to the force needed to break the seal covering the blister in which the tablet is packed.

The friability of the tablets concerned in the invention, measured according to the procedure described in the French Pharmacopoeia, is less than 1%, and preferably less than 0.5%.

The largest dimension of the tablets concerned in the invention may be greater than 5 mm, or even 17 mm, and may reach 25 mm.

Conventional tablets of this size have a tendency to break when they are removed for administration, from the blisters in which they are packed, especially when the blister is composed entirely of a metallic material such as aluminum.

Due to their low friability, breakage of this sort does not occur in the case of tablets according to the invention, which are therefore particularly suitable for packaging in blisters composed entirely of aluminum.

Indeed, the high resistance of the tablets in the invention to breaking enables the risks of tablets breaking to be reduced substantially and enables the tablet to be removed with ease from the blister by tearing, perforating or breaking the seal of the blister by pushing the tablet according to the invention.

In addition, the tablet according to the invention enables child safety standards to be met, as it can be kept in doubly protected blisters, that is to say blisters than can be torn and/or peeled open, and the risk of breakage when removing a tablet from packaging other than a non-peelable blister pack is substantially reduced.

It is therefore possible to package tablets according to the invention in blisters made entirely of aluminum of a substantial thickness providing complete moisture-proofing and thus enabling a commercial product to be obtained which has excellent storage properties.

With regard to the production of tablets according to the invention, the process according to the invention is set out below.

Processes are already known for the production of tablets of conventional composition, which necessarily include the usual and significant quantities of lubricating agent—generally representing 0.5 to 2% of the weight of the tablet—in a mixture with their other constituents. The lubricating agent not only facilitates compression but also aids the flow of the powder mixture. These processes employ devices such as that described in patent EP 673 280, which are suitable for spraying lubricating agent onto the dies of compression machines to limit or prevent sticking of the compression machine.

The tablets obtained by these processes do not exhibit the beneficial properties which were set out above in relation to the tablets according to the invention.

The latter may be obtained by employing the process according to the invention, which consists of the following sequence of steps:
  choosing, firstly, an active substance in the form of coated microcrystals or microgranules, and secondly, a set of excipients including a disintegrating agent, a soluble agent, as well as a lubricating agent;
    mixing the active substance and the excipients with the exception of at least the major part of the lubricating agent;
  feeding a quantity of this mixture necessary to form a tablet into the cavity of a compression device within which the mixture is to be compressed and onto the walls of which the necessary quantity of lubricating agent has been applied in advance;
  compressing the mixture and ejecting the tablet formed.

The process according to the invention has the advantage which arises from the fact that the compression forces that need to be applied to obtain the tablet are appreciably lower than those used in known processes, yet resulting in a hardness that is equal to or even greater than that of conventional tablets.

According to a preferred embodiment of the process according to the invention, the compression forces are in the range 3 kN to 50 kN, preferably in the range 4 kN to 40 kN, and more preferably still, in the range 5 kN to 25 kN.

Even with these compression forces, it is possible to obtain large-sized tablets with a hardness greater than 20 N, and preferably greater than 40 N, and more preferably still, greater than 80 N.

It must be stated in addition that with prior art tablets, it is necessary to modify the quantity of lubricating agent incorporated in the mixture of excipients depending on the active substance used in the tablet. In contrast, and in an entirely advantageous way, the process according to the invention does not require this sort of modification of the formulation of the excipient mixture depending on the active substance used.

The invention can be better understood with the aid of non-limiting examples which are given below and which relate to advantageous embodiments of the invention.

EXAMPLE 1

Paracetamol 500 mg Tablet

Table 1 shows the content per tablet and the percentage composition of this tablet.

TABLE 1

| CONSTITUENTS | CONTENT PER TABLET | PERCENTAGE COMPOSITION |
|---|---|---|
| Coated paracetamol | 548.70 | 39.17 |
| Mannitol for direct compression | 514.80 | 36.74 |
| Mannitol crystalline powder | 171.50 | 12.24 |
| Crospovidone | 120.00 | 8.57 |
| Aspartame | 40.00 | 2.86 |
| Blackcurrant flavor | 5.00 | 0.36 |
| Magnesium stearate | 0.90 | 0.06 |
| TOTAL | 1400.70 mg | 100.0% |

This tablet is produced as described below.

The microcrystals of paracetamol are fed into a fluid-bed plant and a dispersion of EUDRAGIT E 100, EUDRAGIT NE 30 D and colloidal silica in ethanol is sprayed onto the microcrystals to obtain microcrystals coated with 10% of polymer with the formulation given in Table 2 below.

All the excipients are sieved with the exception of the magnesium stearate, and the mixture consisting of the coated paracetamol and the excipients is homogenized in a dry mixer.

The next step is compression on a compression machine fitted with 17 mm diameter dies and punches; the walls of the dies and the punches are first sprayed with magnesium stearate to act as a lubricating agent (the excess quantity of magnesium stearate that does not adhere to the dies and punches is removed by suction before compression).

The compression force is in the range 16 kN to 25 kN, which produces tablets with a hardness of 80 Newtons.

The disintegration time in the mouth, of tablets produced in this way, is less than 30 seconds.

This time corresponds to the length of time between placing the tablet in the mouth when it comes into contact with the saliva, and the moment at which the suspension resulting from the disintegration of the tablet on contact with saliva is swallowed.

Its friability, measured according to the procedure described in the French Pharmacopoeia (10th Edition, V.5.1—Friability of Tablets, January 1993), using a bladed friability tester, is less than 1%.

The quantity of magnesium stearate distributed at the surface of the tablet is 0.9 mg or 0.64 parts per thousand.

TABLE 2

| CONSTITUENTS | CONTENT PER TABLET | PERCENTAGE COMPOSITION |
|---|---|---|
| Coated paracetamol | 500.00 | 91.12 |
| Eudragit NE 30 D, dry | 12.10 | 2.21 |
| Eudragit E 100 | 24.30 | 4.43 |
| Colloidal silica | 12.30 | 2.24 |
| TOTAL | 548.70 mg | 100.0% |

EXAMPLE 2

Ibuprofen 200 mg Tablet

Table 3 shows the unit content of this tablet.

TABLE 3

| CONSTITUENTS | CONTENT PER TABLET | PERCENTAGE COMPOSITION |
|---|---|---|
| Coated ibuprofen granulate | 256.20 | 36.60 |
| Mannitol granulate | 192.80 | 27.54 |
| Mannitol powder | 193.40 | 27.63 |
| Croscarmellose | 21.00 | 3.00 |
| Precipitated silica | 7.00 | 1.00 |
| Aspartame | 25.00 | 3.57 |
| Lemon flavor | 4.00 | 0.57 |
| Magnesium stearate | 0.60 | 0.09 |
| TOTAL | 700.00 mg | 100.00% |

The excipients shown in Table 2 are screened through a sieve with a pore size of 1000 microns.

The various constituents are weighed out into separate containers of appropriate capacity.

The coated ibuprofen granules (whose formulation is given in Table 3 below), mannitol granulate, mannitol powder, croscarmellose, aspartame, precipitated silica and the flavoring are placed one after another in a mixer.

A homogeneous mixture is prepared.

The walls of the dies and the punches of a rotary compression machine are sprayed with magnesium stearate (the excess quantity of magnesium stearate is removed by suction).

The prepared mixture is fed into the dies of the rotary compression machine between the punches covered with magnesium stearate and it is compressed with a compression force of the order of 7 kN, in order to obtain tablets with the following characteristics:

mean tablet weight in the range 665 mg to 735 mg;
breaking strength in the range 20 N to 50 N;
friability less than 1%;
mean disintegration time in the mouth less than 30 seconds.

This disintegration time corresponds to the length of time=between placing the tablet in the mouth when it comes into contact with the saliva, and the moment at which the suspension resulting from the disintegration of the tablet on contact with saliva is swallowed.

The quantity of magnesium stearate in the final tablet is 0.6 mg or 0.8 parts per 1000.

TABLE 4

Formula of ibuprofen-coated granulate

| CONSTITUENTS | CONTENT PER TABLET | PERCENTAGE COMPOSITION |
|---|---|---|
| Ibuprofen | 200.00 | 78.06 |
| Ethylcellulose | 35.00 | 13.66 |
| Precipitated silica | 14.20 | 5.55 |
| HPMC* | 7.00 | 2.73 |
| TOTAL | 256.20 mg | 100.00% |

*HPMC: hydroxypropylmethylcellulose

EXAMPLE 3

Aspirin 500 mg Tablet

Table 5 shows the unit content of this tablet.

TABLE 5

| CONSTITUENTS | CONTENT PER TABLET | PERCENTAGE COMPOSITION |
|---|---|---|
| Coated aspirin granulate | 564.00 | 40.29 |
| Mannitol granulate | 336.00 | 24.00 |
| Mannitol powder | 336.00 | 24.00 |
| Crospovidone | 120.00 | 8.57 |
| Precipitated silica | 14.00 | 1.00 |
| Aspartame | 14.40 | 1.03 |
| Potassium acesulfam | 9.60 | 0.89 |
| Lemon flavor | 5.00 | 0.36 |
| Sodium stearate | 0.90 | 0.06 |
| TOTAL | 1400.00 mg | 100.00% |

The tablets are produced in the same way as in Example 1, using coated granulate with the formulation given in Table 6 below, and by compressing the tablets on a compression machine on which the walls of the dies and the punches have previously been coated by spraying with sodium stearyl fumarate.

TABLE 6

Formula of aspirin-coated granulate

| CONSTITUENTS | CONTENT PER TABLET | PERCENTAGE COMPOSITION |
|---|---|---|
| Aspirin | 500.00 | 88.85 |
| Ethylcellulose | 50.00 | 8.87 |
| HPMC* | 10.00 | 1.77 |
| Colloidal silica | 4.00 | 0.71 |
| TOTAL | 564.00 mg | 100.00% |

*HPMC: hydroxypropylmethylcellulose

The tablets obtained in this manner exhibit the following characteristics:

quantity of sodium stearyl fumarate: 0.9 mg or 0.64 parts per 1000
breaking strength: 30 N to 60 N;
friability: less than 1%;
disintegration time less than 30 seconds.

The invention claimed is:

1. A directly compressible tablet disintegrating in the mouth on contact with saliva in less than 30 seconds, forming an easy-to-swallow suspension and having a friability of less than 1%, said tablet comprising:

a lubricating agent in powder form, and
a dry mixture of an active substance and excipients including a disintegrating agent and a soluble agent with binding properties,
wherein all of the lubricating agent is distributed on the tablet outer surface and the lubricating agent is present in a range of 0.2 to 10 parts per 1000 based on a weight of lubricating agent per total weight of the tablet,
and wherein the active substance is in a form of microcrystals having a continuous polymer coating or of microgranules having a continuous polymer coating.

2. Tablet in accordance with claim 1, wherein a largest dimension of the tablet is greater than 5 mm.

3. Tablet in accordance with claim 1, wherein the lubricating agent is a pharmaceutically acceptable lubricating agent having a melting point of at least 35° C.

4. Tablet in accordance with claim 1, wherein the lubricating agent is a member selected from the group consisting of magnesium stearate, sodium stearyl fumarate, stearic acid and micronized polyoxyethylene glycol.

5. Tablet in accordance with claim 1, wherein the lubricating agent is magnesium stearate.

6. Tablet in accordance with claim 1, wherein the lubricating agent has a particle size distribution less than 30 microns, such that constituent particles of the lubricating agent adhere to a surface when the lubricating agent is sprayed against the surface.

7. Tablet in accordance with claim 1, wherein the disintegrating agent is a member selected from the group consisting of cross-linked sodium carboxymethylcellulose, crospovidone and their mixtures.

8. Tablet in accordance with claim 1, wherein the excipients include a permeabilising agent, a solubilising agent, sweeteners, flavors, and colorings.

9. Tablet in accordance with claim 1, wherein the tablet is packaged in and delivered from blisters composed entirely of aluminium, said blisters optionally including a cover of a plastic material which is to be torn off before opening.

10. Process for producing a tablet in accordance with claim 1, wherein the process comprises:
    choosing, firstly, an active substance in a form of microcrystals having a continuous polymer coating or of microgranules having a continuous polymer coating, and secondly, a set of excipients including a disintegrating agent, a soluble agent with binding properties, and a lubricating agent in powder form;
    dry mixing the active substance and the excipients to form a mixture, provided that the lubricating agent is not included in the mixture;
    applying all of the lubricating agent onto walls surrounding a cavity of a compression device;
    feeding a quantity of the mixture necessary to form a tablet into the cavity of the compression device within which the mixture is to be compressed and onto the walls of which all of the lubricating agent has been applied in advance; and
    compressing the mixture using compression forces and ejecting the tablet formed,
wherein all of the lubricating agent of the tablet thus formed is distributed on the tablet outer surface, and wherein the lubricating agent is present in a range of 0.2 to 10 parts per 1000 based on a weight of lubricating agent per total weight of the tablet.

11. Process in accordance with claim 10, wherein compression forces are in a compression force range from 3 kN to 50 kN.

12. Tablet according to claim 1, wherein the friability of the tablet is less than 0.5%.

13. Tablet in accordance with claim 2, wherein the largest dimension of the tablet is greater than 17 mm.

14. Tablet in accordance with claim 3, wherein the lubricating agent has a melting point higher than 50° C.

15. Tablet in accordance with claim 1, wherein the lubricating agent is present in the range of 3 to 6 parts per 1000 based on a weight of lubricating agent per total weight of the tablet.

16. Tablet in accordance with claim 6, wherein the lubricating agent has a particle size distribution less than 10 microns.

17. Process in accordance with claim 11, wherein the compression force range is 4 kN to 40 kN.

18. Process in accordance with claim 17, wherein the compression force range is 5 kN to 25 kN.

19. Process in accordance with claim 10, wherein the lubricating agent is a member selected from the group consisting of magnesium stearate, sodium stearyl fumarate, stearic acid and micronized polyoxyethylene glycol.

20. Process in accordance with claim 10, wherein the disintegrating agent is a member selected from the group consisting of cross-linked sodium carboxymethylcellulose, crospovidone and their mixtures.

21. Process in accordance with claim 10, wherein the excipients further include a permeabilising agent, a solubilising agent, sweeteners, flavors and colorings.

22. Process for reducing the friability of a directly compressible tablet comprising a step of spraying a lubricating agent on a surface of compression punches such that all of the lubricating agent is distributed on a tablet outer surface, said tablet comprising
    a lubricating agent in powder form, and
    a dry mixture of an active substance and excipients including at least a disintegrating agent, and a soluble agent with binding properties, wherein the active substance is in a form of microcrystals having a continuous polymer coating or of microgranules having a continuous polymer coating
wherein the lubricating agent is present in a range of 0.2 to 10 parts per 1000 based on a weight of lubricating agent per total weight of the tablet.

23. Process in accordance with claim 22, wherein the lubricating agent is a member selected from the group consisting of magnesium stearate, sodium stearyl fumarate, stearic acid and micronized polyoxyethylene glycol.

24. Process in accordance with claim 22, wherein the disintegrating agent is a member selected from the group consisting of cross-linked sodium carboxymethylcellulose, crospovidone and their mixtures.

* * * * *